US012685768B2

(12) United States Patent　　(10) Patent No.: US 12,685,768 B2
Potappel-van 't Land et al.　　(45) Date of Patent: Jul. 21, 2026

(54) NUTRITIONAL COMPOSITION FOR IMPROVING IMMUNE FITNESS

(71) Applicant: N.V. Nutricia, Zoetermeer (NL)

(72) Inventors: Belinda Potappel-van 't Land, Utrecht (NL); Elisabeth Catharina Adriana Maria van Esch, Utrecht (NL); Suzanne Abbring, Utrecht (NL); Johan Garssen, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 1009 days.

(21) Appl. No.: 17/778,008

(22) PCT Filed: Dec. 11, 2020

(86) PCT No.: PCT/EP2020/085752
§ 371 (c)(1),
(2) Date: May 19, 2022

(87) PCT Pub. No.: WO2021/116403
PCT Pub. Date: Jun. 17, 2021

(65) Prior Publication Data
US 2023/0000975 A1　　Jan. 5, 2023

(30) Foreign Application Priority Data
Dec. 11, 2019　(EP) .................................... 19215272

(51) Int. Cl.
| | |
|---|---|
| *A23L 33/00* | (2016.01) |
| *A23L 33/19* | (2016.01) |
| *A61K 9/00* | (2006.01) |
| *A61K 35/20* | (2006.01) |
| *A61K 38/40* | (2006.01) |
| *A61K 39/35* | (2006.01) |
| *A61P 37/00* | (2006.01) |
| *A61P 37/08* | (2006.01) |

(52) U.S. Cl.
CPC ............ *A61K 39/35* (2013.01); *A61K 9/0095* (2013.01); *A61K 35/20* (2013.01); *A61K 38/40* (2013.01); *A61P 37/08* (2018.01)

(58) Field of Classification Search
CPC ...... A61K 39/35; A61K 9/0095; A61K 35/20; A61K 38/40; A61P 37/08; A61P 37/00; A23L 33/40; A23L 33/19
See application file for complete search history.

(56) References Cited

U.S. PATENT DOCUMENTS

2004/0009896 A1　1/2004 Glynn et al.
2015/0246100 A1* 9/2015 Donovan .............. A23L 33/185
　　　　　　　　　　　　　　　　　424/184.1

FOREIGN PATENT DOCUMENTS

| | | |
|---|---|---|
| WO | 2012/077076 A1 | 6/2012 |
| WO | 2012/091921 A1 | 7/2012 |
| WO | WO2012/091921 A | 7/2012 |
| WO | 2014/055748 A1 | 4/2014 |

OTHER PUBLICATIONS

GRAS notification No. 669 (The use of bovine milk drive lactoferrin in determining milk-based infant formulas and toddler formulas; Drummond Food Science Adv Ltd, pp. 1-69, 2016) (Year: 2016).*
Merck manual, Hyper-IgE syndrome accessed Nov. 20, 2021 at URL merckmanuals.com/professional/immunology-allergic-disorders/immunodeficiency-disorders/hyper-ige-syndrome?query=hyper ige syndrome (Year: 2021).*
Zellweger et al., "IgE-associated allergic disorders: recent advances in etiology, diagnosis, and treatment," Allergy European Journal of allergy and clinical immunology 71: 1652-1661 (2016) (Year: 2016).*
Asthma from Merck Manual, pp. 1-19. Accessed Nov. 2, 2017. (Year: 2017).*
Allergic rhinitis from Merck Manual, pp. 1-6. Accessed Nov. 2, 2017. (Year: 2017).*
Overview of Allergic and Atopic Disorders, Merck Manual, Fernandez et al, accessed Sep. 22, 2025 at URL merckmanuals.com/professional/immunology-allergic-disorders/allergic-autoimmune-and-other-hypersensitivity-disorders/overview-of-allergic-and-atopic-disorders, 21 pages (Year: 2025).*
Food allergy, Merck Manual, Fernandez et al, accessed Sep. 22, 2025 at URL merckmanuals.com/professional/immunology-allergic-disorders/allergic-autoimmune-and-other-hypersensitivity-disorders/food-allergy (Year: 2025).*
Legrand, "A critical review of the roles of host lactoferrin in immunity," Biometals 23:365-376 (2010) (Year: 2010).*
Kanagaratham et al, "Experimental models for studying food allergy," Cell Mol Gastroenterol Hapatol 6: 356-369 (2018) (Year: 2018).*
https://www.chondrex.com/blog/ovalbumin-ideal-model-antigen-for-immunology-research.
Kanagaratham, Cynthia, Benjamin F. Sallis, and Edda Fiebiger. "Experimental models for studying food allergy." Cellular and molecular gastroenterology and hepatology 6.3 (2018): 356-369.
Kruzel et al: "Lactoferrin decreases pollen antigen-induced allergic airway inflammation in a murine model of asthma", Immunology, vol. 119, No. 2, Oct. 1, 2006 (Oct. 1, 2006), pp. 159-166, XP055691228, GB. ISSN: 0019-2805, DOI: 10.1111/j.1365-2567.2006.02417.x.
Sherman et al: "Lactoferrin acts as an adjuvant during influenza vaccination of neonatal mice", Biochemical and Biophysical Research Communications, vol. 467, No. 4, Nov. 1, 2015 (Nov. 1, 2015), pp. 766-770, XP055691229, Amsterdam, NL, ISSN: 0006-291X, DOI: 10.1016/j.bbrc.2015.10.067.
Zimecki M et al: "Systemic or local co-administration of lactoferrin with sensitizing dose of antigen enhances delayed type hypersensitivity in mice",Immunology Letters, Elsevier BV, NL, vol. 74, Jan. 1, 2000 (Jan. 1, 2000), pp. 183-188, XP003005416, ISSN: 0165-2478, DOI: 10.1016/50165-2478(00)00260-1.

(Continued)

*Primary Examiner* — Julie Ha
*Assistant Examiner* — Kristina M Hellman
(74) *Attorney, Agent, or Firm* — Ipsilon USA—NLO

(57) ABSTRACT

The present invention relates to a nutritional composition comprising non-denatured lactoferrin for use in preventing or treating allergy, allergic rhinitis, asthma, urticaria, atopic eczema, allergic conjunctivitis, atopic dermatitis or atopic diseases in an infant or a toddler.

16 Claims, No Drawings

(56)　　　　　References Cited

OTHER PUBLICATIONS

Plaut et al: "Lactoferrin" In: "Handbook of proteolytic enzymes : vol. 1 (Third ed.)", Jan. 1, 2013 (Jan. 1, 2013), Academic Press, UK, XPO55692330, ISBN: 978-0-12-382219-2, pp. 3635-3640, DOI: 10.1016/B978-0-12-382219-2.0O805-X.
Oba, Haruka :thèse scientifique japonaise intitulée "Elucidation of the Molecular Mechanism Underlying the Suppressive Effect of Lactoferrin Intake on Atopic Dermatitis", publiée en 2015.
The history of Morinaga Milk : https://ssl.hagukumi.ne.jp/history/.
Morinaga Hagukumi : https://ssl.haqukumi.ne.ip/enq/products/haqukumi/.
GRAS-Notice-GRN-669-Part-1 (2016)—https://www.fda.gov/files/food/published/GRAS-Notice-GRN-669-Part-1.pdf.
EFSA Panel on Dietetic Products, Nutrition and Allergies (NDA). "Scientific Opinion on bovine lactoferrin." EFSA Journal 10.5 (2012): 2701.
Negaoui, Hanane, et al. "Bovine lactoferrin allergenicity as studied in murine model of allergy." Food and Agricultural Immunology 27.5 (2016): 711-723.
Li, Qiuling, et al. "Supplementation transgenic cow's milk containing recombinant human lactoferrin enhances systematic and intestinal immune responses in piglets." Molecular biology reports 41.4 (2014): 2119-2128.
Abe, Hiroaki, et al. "Heat stability of bovine lactoferrin at acidic pH." Journal of Dairy Science 74.1 (1991): 65-71.
USDA database entry for cow milk—FoodData Central Food Details—Milk, whole, 3.25% milkfat, with added vitamin D.
Ono-Ohmachi, Aiko, et al. "Milk basic protein supplementation exerts an anti-inflammatory effect in a food-allergic enteropathy model mouse." Journal of dairy science 101.3 (2018): 1852-1863.
Nutritional profile of AIN-76diet—Product# F1268—Rodent Liquid Diet, AIN-76, Control, 4 Liters/Bag—https://www.bio-serv.com/product/LDAIN76.html.
King Jr, James C., et al. "A double-blind, placebo-controlled, pilot study of bovine lactoferrin supplementation in bottle-fed infants." Journal of pediatric gastroenterology and nutrition 44.2 (2007): 245-251.

Sun, Zhaolin, et al. "Production of hypoallergenic milk from DNA-free beta-lactoglobulin (BLG) gene knockout cow using zinc-finger nucleases mRNA." Scientific Reports 8.1 (2018): 15430.
Similac® Advance® Infant Formula with Iron (2007)—http://rodcon40.ross.com/pn/PediatricProducts.NSF/web_Ross.com_XML_PediatricNutrition.
Fischer, Romy, et al. "Regulation of physiological and pathological Th1 and Th2 responses by lactoferrin." Biochemistry and Cell Biology 84.3 (2006): 303-311.
Zimecki, Michał, et al. "Lactoferrin restrains allergen-induced pleurisy in mice." Inflammation Research 61.11 (2012): 1247-1255.
Kruzel, Marian L., et al. "Lactoferrin decreases pollen antigen-induced allergic airway inflammation in a murine model of asthma." Immunology 119.2 (2006): 159-166.
Wang, S. B., et al. "Lactoferrin administration into the nostril alleviates murine allergic rhinitis and its mechanisms." Scandinavian Journal of Immunology 78.6 (2013): 507-515.
Siqueiros-Cendón, Tania, et al. "Immunomodulatory effects of lactoferrin." Acta Pharmacologica Sinica 35.5 (2014): 557-566.
Dossier « GRAS notice (GRN) No. 465» de la FDA, 21 février2013—https://www.hfpappexternal.fda.gov/scripts/fdcc/index.cfm?set=grasnotices&id=465.
Johnston, William H., et al. "Growth and tolerance of formula with lactoferrin in infants through one year of age: double-blind, randomized, controlled trial." BMC pediatrics 15.1 (2015): 173.
Merrill etal. : USDA Agriculture Handbook No. 74, 1955—https://www.ars.usda.gov/ARSUserFiles/80400525/Data/Classics/ah74.pdf.
Itoh-Nagato, Naoka, et al. "Desensitization to a whole egg by rush oral immunotherapy improves the quality of life of guardians: a multicenter, randomized, parallel-group, delayed-start design study." Allergology International 67.2 (2018): 209-216.
Nowak-Węgrzyn, Anna, and Pantipa Chatchatee. "Mechanisms of tolerance induction." Annals of Nutrition and Metabolism 70.Suppl. 2 (2017): 7-24.

* cited by examiner

NUTRITIONAL COMPOSITION FOR IMPROVING IMMUNE FITNESS

TECHNICAL FIELD OF THE INVENTION

The present invention is in the field of infant nutrition and relates to a nutritional composition for improving immune fitness, said nutritional composition containing non-denatured lactoferrin.

TECHNICAL BACKGROUND OF THE INVENTION

Human milk is the uncontested gold standard concerning infant nutrition. However, in some cases breastfeeding is inadequate or unsuccessful. Also, mothers sometimes are unable to provide breastfeeding. For such situations infant or follow-on formulas have been developed. Commercial infant formulas are commonly used today to provide supplemental or sole source of nutrition early in life. These formulas comprise a range of nutrients to meet the nutritional needs of the growing infant, and typically include fat, carbohydrate, protein, vitamins, minerals, and other nutrients helpful for optimal infant growth and development. Commercial infant formulas are designed to mimic, as closely as possible, the composition and function of human milk.

Immune fitness is a state where an individual's immune system is resilient, having an inbuilt capacity to adapt to challenges by establishing, maintaining and regulating an appropriate immune response. Resilience is the capacity of the immune system to return to homeostasis—a healthy state of wellbeing—after an external challenge. An appropriate response of the immune system is to eliminate a harmful agent, such as bacteria and viruses, but tolerate harmless ones, like food. This immune response should be of an optimal strength: not too weak, which will increase the risk of infections, or too strong, potentially resulting in allergy, chronic inflammation, or autoimmune disorders.

Infants have limited exposure to antigens in utero to induce adaptive immunity. Therefore, in the early phase of life they are thought to be heavily dependent on their innate immune system for protection against infections. Babies who are breastfed have the additional protection of a complex mixture of immune-protective components present in the human milk and colostrum.

The adaptive immune system consists of cell-mediated and antibody-mediated responses. The development of adaptive immune cells in early life is an understudied area of research. Low number of memory effector B cells and effector memory T cells are detected during early infancy. It has been shown that T cells recently produced by the thymus are present in large proportions in the periphery of human infants and these cells are impaired in their acquisition of Th1 function nor have been trained due to relatively limited exposure to foreign structures in the early phase of development. This characteristic contributes to an infant's vulnerability to infections and intracellular pathogens. Studies on cell mediated responses suggest that infants are able to mount T cell responses in most circumstances. However, the magnitude and quality of the response is inferior to those observed in adults. In addition, responses to some vaccines are diminished in Th1 activity and biased towards Th2 function.

The ultimate aim of vaccination is to activate the adaptive immune system inducing highly specific responses against a specific pathogenic agent and generating potent and persistent protective responses. In general terms, antigens (or vaccines) are engulfed by antigen-presenting cells (APCs), and displayed on major histocompatibility complex (MHC) class II and I. The activated APCs alter their surface molecules and begin to release pro-inflammatory signals (cytokines and chemokines), which ideally activate naive T cells that will mature in effector T cells, including Th1 and Th2. Typically, the response to a vaccine/antigen is biased and results in a profile marked by more cellular elements or more humoral elements. It is a misconception that the central aim of vaccination is limited to the expression of antibodies. An effective long-lasting immunization is supported by the cellular response, which plays a central role in the induction of high-affinity antibodies and the immune memory.

Allergy is an abnormal hypersensitivity to a substance which is normally tolerated and generally considered harmless. The first time an allergen meets the immune system, no allergic reaction occurs. Instead, the immune system prepares itself for future encounters with the allergen. The key players in the IgE-mediated allergic cascade are Th2 cells. Th2 cells secrete several cytokines that will activate B lymphocytes to produce antibodies of the subclass E (IgE). IgE antibodies are specific to that particular allergen. The interaction between an allergen and specific IgE antibodies on the surface of effector cells (mast cells and basophils) triggers hypersensitivity responses. This mast cell activation usually occurs within minutes after the second exposure to an allergen. IgE antibodies on mast cells, constructed during the sensitization phase, recognize the allergen and bind to the invader. Once the allergen is bound to the IgE antibody, granules in the mast cells release their contents. These contents, or mediators, are pro-inflammatory substances such as histamine, platelet-activating factor, prostaglandins, cytokines and leukotrienes. These mediators trigger the allergy attack. Histamine stimulates mucus production and causes redness, swelling, and inflammation. Prostaglandins constrict airways and enlarge blood vessels.

The action of environmental factors on an immature, not yet balanced cellular immune system makes young infants especially prone to the development of allergies. Atopic individuals have a tendency to produce more IgE when exposed to certain antigens. Th1 cells and the cytokines released by them are necessary to mount an effective immune response against infection. Th2 cells play a dominant role in IgE production. Both types of T helper cells are reactive to allergens, but at the clonal level, the atopic response is predominantly Th2 as opposed to Th1 cells in non-allergic individuals. During early life, immature mucosal defences permit absorption of allergens, which then act on an immature immune system. In infants, the main exposure is to food allergens, whereas in older children, it is to inhalant allergens. As a consequence, allergy prone children may first suffer IgE-mediated food allergies and eczema. These manifestations may either improve or persist. In older children, asthma and allergic rhinitis provoked by inhalant allergens become predominant.

Strategies to assist specific cellular immune responses at this developmental stage are needed to improve the health of this vulnerable population.

WO 2012/091921 describes the use of nutritional compositions including lactoferrin produced by a non-human source in stimulating innate immune cells, such as macrophages, neutrophils, and dendritic cells.

WO2014/055748 describes a method of increasing immune cell function in a new bom that has not consumed any colostrum or breast milk comprising administering an infant formula comprising 1.0 to about 10 g/L of bovine lactoferrin to the new born mammal. This invention is directed to the innate capacity of the immune response.

WO2012/077076 describes a method of decreasing a subject's risk of developing sensitivity to one or more bovine milk allergens, the method comprising orally administering to the subject one or more bovine milk allergens, wherein the one or more bovine milk allergens is present at a concentration at least 50% greater than the concentration (s) of the milk allergen(s) in whole bovine milk.

Kruzel M L et al. (Lactoferrin decreases pollen antigen-induced allergic airway inflammation in a muine model of asthma, Immunology. 2006) describes that when pollen extract (RWE)-sensitized mice were challenged (intranasally) with RWE robust airway inflammation was observed. When RWE was administered together with LF there was a moderate accumulation of inflammatory cells in the BAL compartment and in the subepithelium.

Sherman M P et al. (Lactoferrin acts as an adjuvant during influenza vaccination of neonatal mice, Biochem Biophys Res Commun. 2015) report a study in which three-day-old mice received subcutaneously 30 micrograms of H1N1 hemagglutinin+200 µg of bovine lactoferrin. The findings suggest that LF enhanced the response to H1N1 hemagglutinin.

SUMMARY OF THE INVENTION

The inventors have found that the administration of a nutritional composition containing non-denatured lactoferrin has an unexpected effect on pediatric subjects in improving specific cellular immune responses, shifting the Th1/Th2 responses towards a Th1-biased response, which culminates in enhanced vaccine specific immune responses and reduced activation of the IgE pathway which is responsible for the clinical signs and symptoms of IgE-mediated allergy and atopic diseases.

Consequently, the administration of a nutritional composition containing non-denatured lactoferrin has a beneficial effect on pediatric subjects in that it enhances (vaccine) specific immune response and further in that it can prevent or reduce the adverse effects of allergy, allergic rhinitis, asthma, urticaria, atopic eczema, allergic conjunctivitis, atopic dermatitis or atopic diseases.

DETAILED DESCRIPTION OF THE INVENTION

Thus, one aspect of the present invention concerns a nutritional composition containing non-denatured lactoferrin for use in the prevention or treatment of allergy, allergic rhinitis, asthma, urticaria, atopic eczema, allergic conjunctivitis, atopic dermatitis or atopic diseases in an infant or a toddler, said nutritional composition being selected from infant formula, follow-on formula and growing-up milk, said nutritional composition comprising 0.03-14 wt. % non-denatured lactoferrin, calculated by weight of total protein.

This aspect of the invention may also be worded as a method for preventing or treating allergy, allergic rhinitis, asthma, urticaria, atopic eczema, allergic conjunctivitis, atopic dermatitis or atopic diseases in an infant or a toddler, comprising administering a nutritional composition comprising 0.03-14 wt. % non-denatured lactoferrin, calculated by weight of total protein, said nutritional composition being selected from infant formula, follow-on formula and growing-up milk.

For some jurisdictions, this aspect of the invention may also be worded as the use of non-denatured lactoferrin or a composition comprising non-denatured lactoferrin, for the manufacture of a nutritional composition for preventing or treating allergy, allergic rhinitis, asthma, urticaria, atopic eczema, allergic conjunctivitis, atopic dermatitis or atopic diseases in an infant or a toddler, said composition being selected from infant formula, follow-on formula and growing-up milk and comprising 0.03-14 wt. % non-denatured lactoferrin, calculated by weight of total protein.

Another aspect of the present invention concerns a nutritional composition containing non-denatured lactoferrin for use in enhancing vaccine specific immune response in an infant or a toddler, said nutritional composition being selected from infant formula, follow-on formula and growing-up milk, said nutritional composition comprising 0.03-14 wt. % non-denatured lactoferrin, calculated by weight of total protein.

This latter aspect of the invention may also be worded as a method for enhancing vaccine specific immune response in an infant or a toddler, comprising administering a nutritional composition comprising 0.03-14 wt. % non-denatured lactoferrin, calculated by weight of total protein, said nutritional composition being selected from infant formula, follow-on formula and growing-up milk.

For some jurisdictions, this latter aspect of the invention may also be worded as the use of non-denatured lactoferrin or a composition comprising non-denatured lactoferrin, for the manufacture of a nutritional composition for enhancing vaccine specific immune response in an infant or a toddler, said composition being selected from infant formula, follow-on formula and growing-up milk and comprising 0.03-14 wt. % non-denatured lactoferrin, calculated by weight of total protein.

The term 'lactoferrin' as used herein refers to a globular glycoprotein with a molecular mass of about 80 kDa that is widely represented in various secretory fluids, such as milk, saliva, tears, and nasal secretions. Lactoferrin can be purified from milk or produced through recombinant DNA technology.

The term "non-denatured lactoferrin" as used herein refers to lactoferrin molecules whose tertiary structure is preserved. Non-denatured lactoferrin is therefor still bioactive.

The term "allergy" as used herein is defined as an abnormal hypersensitivity to a substance which is normally tolerated and generally considered harmless.

In a preferred embodiment the nutritional composition contains 0.06-11 wt. %, preferably 0.09-8 wt. %, more preferably 0.12-6 wt. % non-denatured lactoferrin, calculated by weight of total protein.

Preferably, at least 70 wt. %, more preferably at least 80 wt. %, most preferably at least 90 wt. % of the total lactoferrin in the composition for use according to the invention is non-denatured lactoferrin.

In a preferred embodiment the nutritional composition is a powder. Preferably, the powder is reconstituted with aqueous liquid to prepare a liquid formula and this liquid formula is subsequently orally administered to the infant or the toddler. Preferably, the aqueous liquid is water.

The water content of the nutritional composition typically does not exceed 20 wt. % by total weight. More preferably, the water content does not exceed 15 wt. %, most preferably the water content does not exceed 10 wt. % by total weight.

Preferably, the reconstituted liquid formula has a pH between 6 and 8, more preferably between 6.5 and 7.5.

It is highly desirable that the reconstituted liquid formula comprises 0.005 to 2 g/L, preferably 0.01 to 1.6 g/L, more preferably 0.015 to 1.2 g/L, most preferably 0.02 to 0.8 g/L of non-denatured lactoferrin.

According to a particularly preferred embodiment, the nutritional composition for use according to the invention is administered in liquid form.

The nutritional composition is preferably administered to an infant or a toddler in an amount sufficient to provide 2-2000 mg non-denatured lactoferrin per day, more preferably 6-1400 mg non-denatured lactoferrin per day and most preferably 10-800 mg non-denatured lactoferrin per day.

Expressed differently, the nutritional composition is preferably administered to an infant or a toddler in an amount sufficient to provide 0.2-600 mg non-denatured lactoferrin per kg of bodyweight per day, more preferably 0.6-400 mg non-denatured lactoferrin per kg of bodyweight per day and most preferably 1-250 mg non-denatured lactoferrin per kg of bodyweight per day.

The nutritional composition is preferably administered to an infant or a toddler who has been exclusively formula fed. In other words, the nutritional composition is preferably administered to an infant or toddler who did not drink colostrum and breastmilk.

The nutritional composition is preferably administered to an infant or toddler of at least 1 month old, more preferably to an infant or toddler of at least 2 months old and most preferably to an infant or toddler of at least 4 months old.

The non-denatured lactoferrin is preferably isolated from milk of a non-human animal or produced by a genetically modified organism. More preferably, the non-denatured lactoferrin is non-denatured bovine, caprine or ovine lactoferrin, most preferably non-denatured bovine lactoferrin. Suitable commercial sources of non-denatured bovine lactoferrin are for example MLF-1M by Milei or Bioferrin® 2000 HP by Glanbia Nutritionals.

In a preferred embodiment the nutritional composition is for use in enhancing vaccine specific immune response against antigens of an intracellular pathogen. The intracellular pathogen is preferably a virus, more preferably one or more influenza viruses.

Advantageously, the nutritional composition may be used to enhance vaccine specific immune responses of an infant or toddler vaccinated with inactivated vaccine or sub-unit vaccine. The composition according to the present invention allows for improved specific cellular responses upon challenge in vaccinated paediatric subjects. In view of the vulnerability of these subjects, vaccines of lower reactogenicity such as inactivated instead of attenuated and sub-unit instead of whole pathogen based vaccines are more tolerable and therefore, preferred. In view of the developmental stage of the adaptive immune system of these subjects, the compositions according to the invention are of particular advantage in case these types of vaccines are used.

In a preferred embodiment, the nutritional composition for use in enhancing vaccine specific immune response in an infant or a toddler, is administrated orally to an infant or toddler at least 1 day before the vaccination takes place, more preferably at least 2 days before the vaccination takes place and most preferably at least 7 days before the vaccination takes place.

In a preferred embodiment, the nutritional composition for use in enhancing vaccine specific immune response in an infant or a toddler, is administrated for at least once daily for two consecutive days, more preferably at least once daily for 4 consecutive days and most preferably at least once daily for 7 consecutive days.

In another preferred embodiment the nutritional composition is for use in preventing allergy in infants or toddlers or treating allergen sensitized infants or toddlers. Preferably, the nutritional composition is for use in preventing or treating IgE-mediated allergy. Preferably, the nutritional composition is for use in the prevention or treatment of an allergic response to an allergen originating from food, more preferably to an allergen originating from non-dairy food, most preferably to an allergen originating from a non-dairy food selected from peanut, tree nut, shellfish, wheat, soy, egg and/or sesame.

In yet another preferred embodiment, the nutritional composition is for use in the prevention or treatment of an allergic response to an allergen originating from peanut, tree nut, shellfish, wheat, soy, egg, sesame, pollen, mould or dust mite.

In another more preferred embodiment the nutritional composition is for use in the prevention of allergy, allergic rhinitis, asthma, urticaria, atopic eczema, allergic conjunctivitis, atopic dermatitis or atopic diseases in an infant or a toddler. Preferably the nutritional composition is for use in preventing allergy in infants or toddlers. Typically, the nutritional composition is for use in preventing IgE-mediated allergy.

Preferably, the nutritional composition is for use in the prevention of an allergic response to an allergen originating from food, more preferably to an allergen originating from non-dairy food, most preferably to an allergen originating from a non-dairy food selected from peanut, tree nut, shellfish, wheat, soy, egg and/or sesame.

In yet another more preferred embodiment, the nutritional composition is for use in the prevention of an allergic response to an allergen originating from peanut, tree nut, shellfish, wheat, soy, egg, sesame, pollen, mould or dust mite.

The nutritional composition according to the invention is preferably not fermented.

The nutritional composition advantageously comprises 5-20 cal. % protein, including lactoferrin; 30-60 cal. % lipids; and 25-75 cal. % digestible carbohydrates.

The nutritional composition according to the invention is preferably prepared by a process comprising the steps of:
a. providing a mixture of protein, lipids and digestible carbohydrates;
b. heating said mixture to at least 72° C. to obtain a heated mixture;
c. spray drying said heated mixture to obtain a powdered composition; and
d. dry-blending non-denatured lactoferrin with the powdered composition to obtain the nutritional composition.

Another aspect of the invention relates to a nutritional composition selected from infant formula, follow-on formula and growing-up milk, said nutritional composition comprising
30-80 cal. % lipids,
5-20 cal. % protein and
25-75 cal. % digestible carbohydrates;
wherein the protein comprises (i) 0.03-14 wt. % non-denatured lactoferrin calculated by weight of total protein and (ii) one or more protein allergens selected from peanut protein, tree nut protein, shellfish protein, gluten, soy protein, egg protein or sesame protein.

Preferably the protein comprises 0.06-11 wt. %, more preferably 0.09-8 wt. %, most preferably 0.12-6 wt. % non-denatured lactoferrin, calculated by weight of total protein.

Preferably, the non-denatured lactoferrin is non-denatured bovine, caprine or ovine lactoferrin, most preferably non-denatured bovine lactoferrin.

The protein allergen in the nutritional composition may be intact, partially hydrolyzed or extensively hydrolyzed. The term "degree of hydrolysis" refers to the extent to which peptide bonds are broken by a hydrolysis method. The term "partially hydrolyzed" means having a degree of hydrolysis which is greater than 0% but less than about 50%. The term "extensively hydrolyzed" means having a degree of hydrolysis which is greater than or equal to about 50%.

Preferably, the protein allergen is intact or partially hydrolyzed. Typically, the degree of hydrolysis is between 0-50%, more preferably between 5-40%, most preferably between 10-30%.

The nutritional composition preferably contains 0.01-50 mg of protein allergen per gram of protein, more preferably 0.05-10 mg of protein allergen per gram of protein and most preferably 0.1-5 mg of protein allergen per gram of protein.

The aforementioned nutritional composition may be administered to infants or toddlers to reduce the risk that such infants or toddlers will develop an allergy for the one or more protein allergens contained therein. Preferably, the aforementioned nutritional composition is for use in the prevention of food allergy. More preferably, said composition is for use in the prevention of the development of a food allergy in infants or toddlers that have not yet been exposed to the one or more protein allergens contained therein.

Lipid

The nutritional composition comprises lipid. Lipid in the present invention comprises one or more selected from the group consisting of triglycerides, polar lipids (such as phospholipids, cholesterol, glycolipids, sphingomyelin), free fatty acids, monoglycerides and diglycerides.

The lipid provides preferably 30 to 60% of the total calories of the nutritional composition. More preferably the nutritional composition comprises lipid providing 35 to 55% of the total calories, even more preferably the nutritional composition comprises lipids providing 40 to 50% of the total calories. The lipids are preferably present in an amount of 3 to 7 g per 100 kcal, more preferably in an amount of 4 to 6 g lipid per 100 kcal and most preferably in an amount of 4.5 to 5.5 g lipid per 100 kcal. When in liquid form, e.g. as a ready-to-feed liquid, the nutritional composition preferably comprises 2.1 to 6.5 g lipids per 100 ml, more preferably 3.0 to 4.0 g per 100 ml. Based on dry weight the nutritional composition preferably comprises 10 to 50 wt. %, more preferably 12.5 to 40 wt. % lipids, even more preferably 19 to 30 wt. % lipids.

The lipid preferably comprises vegetable lipids. The presence of vegetable lipids advantageously enables an optimal fatty acid profile high in polyunsaturated fatty acids and/or more reminiscent to human milk fat. Lipid from non-human mammalian milk alone, e.g. cow's milk, does not provide an optimal fatty acid profile. The amount of essential fatty acids is too low in non-human mammalian milk.

Preferably the nutritional composition comprises at least one, preferably at least two vegetable lipid sources selected from the group consisting of linseed oil (flaxseed oil), rape seed oil (such as colza oil, low erucic acid rape seed oil and canola oil), sunflower oil, high oleic sunflower oil, safflower oil, high oleic safflower oil, olive oil, coconut oil, palm oil and palm kernel oil.

In a preferred embodiment, the nutritional composition comprises 5 to 100 wt. % vegetable lipids based on total lipids, more preferably 10 to 95 wt. %, more preferably 20 to 80 wt. %, even more preferably 25 to 75 wt. %, most preferably 40 to 70 wt. % vegetable lipids based on total lipids. It is noted therefore that the nutritional composition also may comprise non-vegetable lipids. Non-vegetable lipids may include mammalian milk fat, mammalian milk derived lipid as a preferred source of phospholipid, and fish, marine and/or microbial oils as source of long chain poly-unsaturated fatty acids (LC-PUFA).

Triglycerides are the major fraction of the lipids in the nutritional composition. Triglycerides comprise a glycerol moiety to which, via ester bonds, three fatty acid residues are attached, which may be the same or different, and which are generally chosen from saturated and unsaturated fatty acids containing 4 to 26 carbon atoms. Such triglycerides may differ in the fatty acid residues that are present and/or may differ in the respective position(s) of the fatty acid residues to the glycerol backbone (e.g. in the sn-1, sn-2 and/or sn-3 position). Preferably the nutritional composition comprises at least 70 wt. %, more preferably at least 80 wt. %, more preferably at least 85 wt. % triglycerides based on total lipids, even more preferably at least 90 wt. % triglycerides based on total lipids, and most preferably at least 95 wt. % triglycerides based on total lipids.

Lipids that can be used to enhance the amount of PA located at the sn-2 position in triglycerides based on total PA are commercially available—e.g. from Loders Croklaan under the name Betapol™ and/or can be prepared in a manner known per se, for instance as described in EP 0698078 and/or EP 0758846. Another suitable source is InFat™ of Enzymotec. In case these lipids are obtained by trans- or interesterification of vegetable triglycerides, these sources are in the context of the present invention regarded as vegetable lipids.

A preferred source for triglycerides to enhance PA at the sn-2 or beta position in a triglyceride is non-human animal fat, more preferably non-human mammalian milk fat, even more preferably cow's milk fat. Preferably non-human mammalian milk fat, in particular cow's milk fat, is used in the form of anhydrous milk fat, butter oil, butterfat or butter. Preferably, the source of the milk fat is in a homogenous fat phase, such as butter oil or anhydrous milk fat, and not in the form of oil in water emulsion such as cream.

Preferably the amount of the source of lipid, which comprises triglycerides with an increased amount of palmitic acid residues in the sn-2 position of a triglyceride, that is comprised in the lipid of the nutritional composition, is between 10 and 70 wt. %, more preferably between 20 and 65 wt. %, even more preferably between 30 and 60 wt. % based on total lipid. Such source of lipid is preferably mammalian milk fat, more preferably such source of lipids is non-human mammalian milk fat. The mammalian milk fat is preferably selected from butter, butter fat, butter oil or anhydrous milk fat. Preferably the nutritional composition comprises mammalian milk fat selected from butter, butter fat, butter oil or anhydrous milk fat between 10 and 70 wt. % based on total lipid, more preferably between 20 and 75 wt. %, even more preferably between 30 and 60 wt. % based on total lipid.

In a particularly preferred embodiment, the lipid in the nutritional composition comprises:

a. 30 to 90 wt. % vegetable fat based on total lipid, and b. 10 to 70 wt. % mammalian milk fat based on total lipid, wherein the mammalian milk fat is selected from butter, butter fat, butter oil or anhydrous milk fat.

More preferably, the lipid in the nutritional composition comprises:

a. 35 to 80 wt. % vegetable fat based on total lipid, and b. 20 to 65 wt. % mammalian milk fat based on total lipid, wherein the mammalian milk fat is selected from butter, butter fat, butter oil or anhydrous milk fat.

Most preferably, the lipid in the nutritional composition comprises:

a. 40 to 70 wt. % vegetable fat based on total lipid, and b. 30 to 60 wt. % mammalian milk fat based on total lipid, wherein the mammalian milk fat is selected from butter, butter fat, butter oil or anhydrous milk fat.

In a preferred embodiment, the lipid comprises at least 10 wt. % palmitic acid (PA) based on total fatty acids and at least 15 wt. % of palmitic acid, based on total palmitic acid, is located at the sn-2 position of a triglyceride.

The lipids in the nutritional composition are preferably chosen such that the amount of palmitic acid (PA) that is present in the total lipid of the nutritional composition is at least 10 wt. % based on total fatty acids in the total lipid, preferably at least 15 wt. %. Preferably the amount of PA that is present in the total lipid is below 30 wt. % based on total fatty acids. More preferably the amount of PA that is present in the lipid is from 12 to 26 wt. % based on total fatty acids in the total lipid, even more preferably from 14 to 24 wt. %, even more preferably from 16 to 22 wt. %.

The lipids in the nutritional composition are preferably chosen such that, based on the total PA present in the lipid, at least 15 wt. %, preferably at least 20 wt. %, more preferably at least 25 wt. %, more preferably at least 30 wt. % PA is in the sn-2 or beta position in a triglyceride. Preferably the amount of PA in the sn-2 position in a triglyceride is not more than 45 wt. %, preferably not more than 40 wt. % based on total PA present in the lipid. Preferably the amount of PA in the sn-2 position in a triglyceride is from 25 to 40 wt. % based on total PA present in the total lipid.

SFA relates to saturated fatty acids and/or acyl chains, MUFA relates to mono-unsaturated fatty acid and/or acyl chains, PUFA refers to polyunsaturated fatty acids and/or acyl chains with 2 or more unsaturated bonds; LC-PUFA refers to long chain polyunsaturated fatty acids and/or acyl chains comprising at least 20 carbon atoms in the fatty acyl chain and with 2 or more unsaturated bonds; Medium chain fatty acids (MCFA) refer to fatty acids and/or acyl chains with a chain length of 6, 8 or 10 carbon atoms. n3 or omega-3 PUFA refers to polyunsaturated fatty acids and/or acyl chains with 2 or more unsaturated bonds with an unsaturated bond at the third carbon atom from the methyl end of the fatty acyl chain, n6 or omega-6 PUFA refers to polyunsaturated fatty acids and/or acyl chains with 2 or more unsaturated bonds with an unsaturated bond at the sixth carbon atom from the methyl end of the fatty acyl chain.

DHA refers to docosahexaenoic acid and/or acyl chain (22:6, n3); DPA refers to docosapentaenoic acid and/or acyl chain (22:5 n3). EPA refers to eicosapentaenoic acid and/or acyl chain (20:5 n3); ARA refers to arachidonic acid and/or acyl chain (20:4 n6). LA refers to linoleic acid and/or acyl chain (18:2 n6); ALA refers to alpha-linolenic acid and/or acyl chain (18:3 n3). PA relates to palmitic acid and/or acyl chains (C16:0). BA refers to butyric acid (4:0).

The nutritional composition according to the present use preferably comprises LA. LA is an n6 PUFA and the precursor of n6 LC-PUFA and is an essential fatty acid as it cannot be synthesized by the human body. LA preferably is present in a sufficient amount in order to promote a healthy growth and development, yet in an amount as low as possible to prevent negative, competitive, effects on the formation of n3 PUFA and a too high n6/n3 ratio. The nutritional composition therefore preferably comprises less than 15 wt. %, more preferably less than 12 wt. %, more preferably less than 10 wt. % LA based on total fatty acids. The nutritional composition preferably comprises at least 5 wt. % LA based on fatty acids, preferably at least 6 wt. % LA, more preferably at least 7 wt. % LA based on total fatty acids.

The nutritional composition preferably comprises ALA. ALA is a n3 PUFA and the precursor of n3 LC-PUFA and is an essential fatty acid as it cannot be synthesized by the human body. Preferably ALA is present in a sufficient amount to promote a healthy growth and development of the infant. The nutritional composition therefore preferably comprises at least 1.0 wt. %, more preferably the nutritional composition comprises at least 1.5 wt. %, even more preferably at least 2.0 wt. % ALA based on total fatty acids. Preferably the nutritional composition comprises less than 10 wt. % ALA, more preferably less than 5.0 wt. % based on total fatty acids.

The weight ratio LA/ALA preferably is well balanced in order to ensure an optimal n6/n3 PUFA, n6/n3 LC PUFA and DHA/ARA ratio in the cellular membranes. Therefore, the nutritional composition preferably comprises a weight ratio of LA/ALA from 2 to 20, more preferably from 3 to 15, more preferably from 5 to 12, more preferably from 5 to 10. Preferably the n6 PUFA/n3 PUFA weight ratio is from 3 to 20, more preferably from 3 to 15, more preferably from 5 to 12, more preferably from 5 to 10.

Preferably, the nutritional composition comprises n3 LC-PUFA, such as EPA, DPA and/or DHA, more preferably DHA. As the conversion of ALA to DHA may be less efficient in infants, preferably both ALA and DHA are present in the nutritional composition. Preferably the nutritional composition comprises at least 0.05 wt. %, preferably at least 0.1 wt. %, more preferably at least 0.2 wt. %, of DHA based on total fatty acids. Preferably the nutritional composition comprises not more than 2.0 wt. %, preferably not more than 1.0 wt. % of DHA based on total fatty acids.

The nutritional composition preferably comprises ARA. Preferably the nutritional composition comprises at least 0.05 wt. %, preferably at least 0.1 wt. %, more preferably at least 0.2 wt. % of ARA based on total fatty acids. As the group of n6 fatty acids, especially arachidonic acid (ARA) counteracts the group of n3 fatty acids, especially DHA, the nutritional composition preferably comprises relatively low amounts of ARA. Preferably the nutritional composition comprises not more than 2.0 wt. %, preferably not more than 1.0 wt. % of ARA based on total fatty acids. Preferably the weight ratio between DHA and ARA is between 1:4 to 4:1, more preferably between 1:2 to 2:1, more preferably between 0.6 and 1.5.

Digestible Carbohydrates

The nutritional composition comprises digestible carbohydrates. The digestible carbohydrates preferably provide 25 to 75% of the total calories of the nutritional composition. Preferably the digestible carbohydrates provide 40 to 60% of the total calories. Based on calories the nutritional composition preferably comprises of 5 to 20 g of digestible carbohydrates per 100 kcal, more preferably 6 to 16 g per 100 kcal. When in liquid form, e.g. as a ready-to-feed liquid, the nutritional composition preferably comprises 3 to 30 g digestible carbohydrate per 100 ml, more preferably 6 to 20, even more preferably 7 to 10 g per 100 ml. Based on dry weight the nutritional composition preferably comprises 20 to 80 wt. %, more preferably 40 to 65 wt. % digestible carbohydrates.

Preferred digestible carbohydrate sources are lactose, glucose, sucrose, fructose, galactose, maltose, starch and maltodextrin. Lactose is the main digestible carbohydrate present in human milk. Lactose advantageously has a low glycaemic index. The nutritional composition preferably comprises lactose. The nutritional composition preferably comprises digestible carbohydrate, wherein at least 35 wt. %, more preferably at least 50 wt. %, more preferably at least 75 wt. %, even more preferably at least 90 wt. %, most preferably at least 95 wt. % of the digestible carbohydrate is lactose. Based on dry weight the nutritional composition preferably comprises at least 25 wt. % lactose, preferably at least 40 wt. % lactose.

Protein

The nutritional composition comprises protein. The protein preferably provides 5 to 20% of the total calories. Preferably the nutritional composition comprises protein that provides 6 to 12% of the total calories. Preferably the nutritional composition comprises less than 3.5 g protein per 100 kcal, more preferably the nutritional composition comprises between 1.5 and 2.1 g protein per 100 kcal, even more preferably between 1.6 and 2.0 g protein per 100 kcal. A low protein concentration advantageously is closer to human milk as human milk comprises a lower amount of protein based on total calories compared to cow's milk. The protein concentration in a nutritional composition is determined by the sum of protein, peptides and free amino acids. Based on dry weight the nutritional composition preferably comprises less than 12 wt. % protein, more preferably between 9.6 and 12 wt. %, even more preferably between 10 and 11 wt. %. Based on a ready-to-drink liquid product the nutritional composition preferably comprises less than 1.5 g protein per 100 ml, more preferably between 1.2 and 1.5 g, even more preferably between 1.25 and 1.35 g per 100 ml.

The source of the protein should be selected in such a way that the minimum requirements for essential amino acid content are met and satisfactory growth is ensured. Hence protein sources based on cows' milk proteins such as whey, casein and mixtures thereof and proteins based on soy, potato or pea are preferred. In case whey proteins are used, the protein source is preferably based on acid whey or sweet whey, whey protein isolate or mixtures thereof. Preferably the nutritional composition comprises at least 3 wt. % casein based on dry weight. Preferably the casein is intact and/or non-hydrolyzed.

Non-Digestible Carbohydrates

In one embodiment the nutritional composition preferably comprises non-digestible oligosaccharides. Preferably the nutritional composition comprises non-digestible oligosaccharides with a degree of polymerization (DP) between 2 and 250, more preferably between 3 and 60.

Preferably the nutritional composition comprises fructo-oligosaccharides, galacto-oligosaccharides and/or galacturonic acid oligosaccharides, more preferably fructo-oligosaccharides and/or galacto-oligosaccharides, even more preferably galacto-oligosaccharides, most preferably trans-galacto-oligosaccharides. In a preferred embodiment the nutritional compostions comprises a mixture of galacto-oligosaccharides and fructo-oligosaccharides, more preferably transgalacto-oligosaccharides and fructo-oligosaccharides. Suitable non-digestible oligosaccharides are for example VIvinaW®GOS (FrieslandCampina DOMO), Raftilin®HP or Raftilose® (Oraft).

Preferably, the nutritional composition comprises 80 mg to 2 g non-digestible oligosaccharides per 100 ml, more preferably 150 mg to 1.5 g, even more preferably 300 mg to 1 g per 100 ml. Based on dry weight, the nutritional composition preferably comprises 0.25 wt. % to 20 wt. %, more preferably 0.5 wt. % to 10 wt. %, even more preferably 1.5 wt. % to 7.5 wt. % of non-digestible oligosaccharides.

Formula

The use according to the present invention requires the administration of an infant formula, a follow-on formula or a growing-up milk. This means that the composition that is administered is not human milk. It also means that the composition that is administered is not native cow's milk or native milk from another mammal. Alternatively, the terms as used herein, "infant formula" or "follow-on formula" or "growing-up milk" means that it concerns a composition that is artificially made or in other words that it is synthetic. Hence in one embodiment, the nutritional composition that is administered is an artificial infant formula or an artificial follow-on formula or an artificial growing-up milk or a synthetic infant formula or a synthetic follow-on formula or a synthetic growing-up milk.

In the present context, infant formula refers to nutritional compositions, artificially made, intended for infants of 0 to about 4 to 6 months of age and are intended as a substitute for human milk. Typically, infant formulae are suitable to be used as sole source of nutrition. Such infant formulae are also known as starter formula. Follow-on formula for infants starting with at 4 to 6 months of life to 12 months of life are intended to be supplementary feedings to infants that start weaning on other foods. Infant formulae and follow-on formulae are subject to strict regulations, for example for the EU regulations no. 609/2013 and no. 2016/127. In the present context, growing-up milk refers to nutritional compositions, artificially made, intended for infants of 12 months to 36 months, which are intended to be supplementary feedings to infants.

The nutritional composition is preferably an infant formula or a follow-on formula. More preferably the nutritional composition is an infant formula.

The nutritional composition is preferably an infant formula or follow-on formula and preferably comprises 3 to 7 g lipid/100 kcal, preferably 4 to 6 g lipid/100 kcal, more preferably 4.5 to 5.5 g lipid/100 kcal, preferably comprises 1.7 to 3.5 g protein/100 kcal, more preferably 1.8 to 2.1 g protein/100 kcal, more preferably 1.8 to 2.0 g protein/100 kcal and preferably comprises 5 to 20 g digestible carbohydrate/100 kcal, preferably 6 to 16 g digestible carbohydrate/100 kcal, more preferably 10 to 15 g digestible carbohydrate/100 kcal.

Preferably the nutritional composition is an infant formula or follow-on formula, has an energy density of 60 kcal to 75 kcal/100 ml, more preferably 60 to 70 kcal/100 ml, when in a ready-to-drink form. This density ensures an optimal balance between hydration and caloric intake.

The invention is further illustrated by the following non-limiting examples.

EXAMPLES

Example 1—Effect of a Nutritional Composition Comprising Lactoferrin Studied in a Vaccinated Animal Model Six-week-old old male specific pathogen-free inbred mice were obtained from Harlan (the Netherlands) and housed under standard housing conditions with a 12 h dark and light cycle. All animals had free access to tap water and the semi-purified AIN-93G diet (Research Diet Services, Wijk bij Duurstede, the Netherlands). The study protocol was reviewed and approved by the Animal Experimental Committee of the Utrecht University.

The vaccination experiment was performed using Influvac (Solvay Pharmaceuticals, Weesp, the Netherlands) from season 2002/2003. It is an inactivated influenza virus vaccine based on isolated haemagglutinin (HA) and neuraminidase antigens of three strains of myxovirus influenza, in a dose equivalent to 30 μg/mL HA per strain (90 μg/mL HA in total). An oil-adjuvant was used in all vaccinations (Stimune, previously known as Specol; Cedi-diagnostics, Lelystad, The Netherlands).

The mice were divided in 4 groups according to the table below:

| Group (n = 10) | Vaccine | Lactoferrin |
| --- | --- | --- |
| Control | No (PBS) | No (PBS) |
| Control + LF | No (PBS) | Yes |
| Vaccinated | Yes | No (PBS) |
| Vaccinated + LF | Yes | Yes |

The mice groups "Control+LF" and "Vaccinated+LF" received oral gavage once daily with a dosage of 200 ug/day for 1 week (7 days) prior to the primary vaccination.

The mice from groups "Vaccinated" and "Vaccinated LF" received a primary vaccination (day 0) and a booster vaccination, consisting of a subcutaneous (sc) injection of a 1:1 mix of vaccine and adjuvant in a total volume of 100 μL. The booster vaccination was given 21 days after the primary vaccination.

The experiments ended 10 days after booster vaccination. Blood samples (taken by retro-orbital puncture) were taken at the end of the experiment, centrifuged, after which the serum was collected and stored at −80° C. until use.
Delayed Type Hypersensitivity (DTH)

Vaccine-specific DTH reactions were induced 9 days after the last vaccination, by subcutaneous injection of 25 μL Influvac (30 μg/mL per haemagglutinin subunit) into the ear pinnea of one ear. As control, the other ear was injected with 25 μL PBS. Ear thickness was measured in duplicate before challenge, and 24 hours thereafter, with a digital micrometer (Mitutoyo Digimatic 293561, Veenendaal, the Netherlands). The influvac specificity of the DTH response was calculated by subtracting the basal ear thickness from the value at 24 hours after challenge and was corrected for the control swelling.
Evaluation of Antibody Responses in Serum Serum antibody concentrations were measured by ELISA. In short, 96-well plates (Costar EIA/RIA plate, Alphen a/d Rijn, The Netherlands) were coated with 1:100 diluted Influvac in PBS. Blocking reagent was 2% BSA (Sigma, Zwijndrecht, The Netherlands) in PBS. A dilution series of pooled serum that contained anti-vaccine antibodies was added for standard curve calculation. Anti-IgG-HRP (Santa Cruz Biotechnology, Heerhugowaard, The Netherlands), anti-IgG2a-biotin (Becton Dickinson, Heerhugowaard, The Netherlands) antibodies were diluted 1:1000 in dilution buffer. For the biotin-conjugated antibodies, the plates were subsequently incubated with a 1:20,000 dilution of strepta-vidin-HRP (Biosource, Etten-Leur, The Netherlands). Plates were incubated with ready-to-use TMB substrate (Perbio Science, Etten-Leur, The Netherlands) and were measured in a Bio-Rad Ultramark plate reader. Concentrations in test sera were calculated in arbitrary units (AU), relative to the standard curve of the diluted pooled serum. The concentration of the pooled serum was defined as 1000 AU/mL.
Statistical Analyses All statistical calculations were performed using SPSS version 12.0.1 software. Statistical differences between test and control groups were analyzed by T-test. All values are presented as Mean t SD. P-values <0.05 were considered significant.
Results

| Group | DTH (mean ± SD) | IgG2a (mean ± SD) |
| --- | --- | --- |
| Control | 0.5 ± 0.3 | 0 |
| Control + LF | 0.8 ± 0.4 | 0 |
| Vaccinated | 8.8 ± 1.2 | 180 ± 15 |
| Vaccinated + LF | 14.7 ± 1.3 | 290 ± 75 |

Vaccinated mice receiving lactoferrin (group Vaccinated+LF) showed significantly (p<0.05) increased expression of influenza specific IgG2a in serum as compared to vaccinated mice receiving PBS (group Vaccinated).

Vaccinated mice receiving lactoferrin (group Vaccinated+LF) showed significantly (P<0.01) increased influenza-specific DTH responses as compared to vaccinated mice receiving PBS (group Vaccinated).

These findings demonstrate a clear enhancement of specific cellular immune responses, more specifically Th1 responses, in vaccinated subjects receiving lactoferrin orally.

Example 2—Effect of a Nutritional Composition
Comprising Lactoferrin and the Development of
Allergy Symptoms in an Animal Model Previously, it was demonstrated that raw cow's milk has the capacity to prevent the development of OVA-induced food allergy in a murine animal model. This protective effect was lost once the milk was heat-treated, e.g. by pasteurization, such as in shop milk.
Animals Three-week-old, specific pathogen-free, female C3H/HeOuJ mice (The Jackson Laboratory, Bar Harbor, ME, USA) were housed at the animal facility of Utrecht University (Utrecht, The Netherlands) in filter-topped makrolon cages (one cage/group, n=6-8/cage) with standard chip bedding, Kleenex tissues and a plastic shelter, on a 12 h light/dark cycle with access to food ('Rat and Mouse Breeder and Grower Expanded'; Special Diet Services, Witham, UK) and water ad libitum. Upon arrival, mice were randomly assigned to the control and experimental groups and were habituated to the laboratory conditions for six days prior to the start of the study. All animal procedures were approved by the Ethical Committee for Animal Research of the Utrecht University and were compiled with the European Directive 2010/63/EU on the protection of animals used for scientific purposes (AVD108002015346).
Experimental Design—Tolerance Induction, Sensitization and Challenges Prior to sensitization, mice were orally treated with 0.5 mL PBS (as a control), raw milk, shop milk or shop milk spiked with LF for eight consecutive days (days −9 to −2). On experimental days 0, 7, 14, 21 and 28, mice (n=8/group) were orally sensitized, by using a blunt needle, to the hen's egg protein OVA (20 mg/0.5 mL PBS; grade V; Sigma-Aldrich) using cholera toxin (CT; 15 μg/0.5 mL PBS; List Biological Laboratories, Campbell, CA, USA) as an adjuvant. Sham-sensitized control mice (n=6) received CT alone (15 µg/0.5 mL PBS). To remove lipopolysaccharide, OVA solutions were passed through Pierce High Capacity Endotoxin Removal Resin (Thermo Fisher Scientific, Paisley, Scotland) prior to use. On day 33, five days after the last sensitization, all mice were challenged intradermally in both ear pinnae with OVA (10 µg/20 µL PBS) to determine the acute allergic response.

So, there were 4 test groups:

| Group | N | Tolerance induction (days: −9 to −2) | Sensitization (days: 0, 7, 14, 21, 28) | Intradermal challenge (day 33) |
|---|---|---|---|---|
| PBS | 6 | PBS | PBS + CT | OVA |
| Raw milk | 8 | Raw milk | OVA + CT | OVA |
| Shop milk | 8 | Shop milk | OVA + CT | OVA |
| Shop milk + lactoferrin | 8 | Shop milk + lactoferrin | OVA + CT | OVA |

Milk Types and Bioactive Whey Proteins

Raw, unprocessed, cow's milk was collected from a biodynamic dairy farm legally allowed to sell raw milk (organic 'Vorzugsmilch' (15); Hof Dannwisch, Horst, Germany). Shop milk (full fat, store-bought, milk) was obtained from Melkan Superunie (Beesd, The Netherlands). On the days of milk treatment, part of the shop milk was spiked (0.325 mg/0.5 mL shop milk) with the bioactive whey protein lactoferrin (LF). Bovine milk LF was obtained from Synlait Milk (Canterburg, New Zealand). Mice (about 25 grams) received 8 dosages of 0.5 ml LF spiked milk.

Evaluation of the Acute Allergic Response

To assess the severity of the acute allergic symptoms upon intradermal challenge in both ear pinnae with OVA, the acute allergic skin response, anaphylactic shock symptoms were evaluated by a researcher blinded to treatment. The acute allergic skin response, expressed as Δ ear swelling (µm), was calculated by subtracting the mean basal ear thickness from the mean ear thickness measured 1 h after intradermal challenge. Ear thickness at both timepoints was measured in duplicate for each ear using a digital micrometer (Mitutoyo, Veenendaal, The Netherlands). To perform the intradermal challenge and both ear measurements, mice were anesthetized using inhalation of isoflurane (Abbott, Breda, The Netherlands). The severity of the anaphylactic shock symptoms was scored 45 min after the intradermal challenge by using a previously described, validated, scoring table (Xi X M et al., J Allergy Clin Immunol (1999) 103(2 Pt 1): 206-14).

Statistical Analysis

Significant outliers were excluded based on the Grubbs' test. The acute allergic skin response was analyzed with one-way ANOVA followed by Bonferroni's multiple comparisons test for pre-selected groups. The anaphylactic shock symptoms were analyzed with the Kruskal-Wallis test for non-parametric data followed by Dunn's multiple comparisons test for pre-selected groups. Statistical analyses were performed using GraphPad Prism software (version 7.03; GraphPad Software, San Diego, CA, USA) and results were considered statistically significant when P<0.05.

Results

In mice treated with raw milk prior to OVA sensitization, the acute allergic skin response and anaphylactic shock score were reduced compared to mice treated with shop milk. In both cases the reduction was statistically significant different with a p-value below 0.005.

Spiking shop milk with LF significantly reduced the acute allergic skin response compared to shop milk-treated mice (p<0.01). Spiking shop milk with LF also significantly lowered the anaphylactic shock score compared to shop milk treated mice (p<0.01).

| Group | Acute allergic skin response (mean + SEM) | Anaphylactic shock score (score per mouse) |
|---|---|---|
| PBS | 30.8 (6.9) | 0, 0, 0, 0, 0, 0 |
| Raw milk | 59.7 (9.0) | 0, 0, 0, 0, 0, 0, 0, 0 |
| Shop milk | 138.6 (8.0) | 2, 1, 2, 3, 2, 0, 0, 2 |
| Shop milk + lactoferrin | 65.6 (17.3) | 0, 0, 1, 1, 0, 0, 1 (−1 outlier) |

These findings demonstrate that non-denatured lactoferrin is capable of suppressing OVA-induced allergic symptoms.

Example 3—Infant Formula Comprising Non-Denatured Lactoferrin

A mixture of ingredients was provided for preparing an infant formula comprising per 100 ml (66 kcal), 1.5 g protein (cow's milk derived protein, with whey protein and casein in a weight ratio of 6:4), 7 g digestible carbohydrates (mainly lactose), 3.4 g lipid of which vegetable fat (palm oil, low erucic acid rape seed oil, sunflower oil, coconut oil, high oleic acid sunflower oil, soy lecithin) and fish oil and microbial oil as a source of LC-PUFA, 0.8 g non-digestible oligosaccharides (trans galacto-oligosaccharides and long chain fructo oligosaccharide). Minerals, vitamins trace elements and other micronutrients were present as known in the art and in compliance with directives for infant formula.

This mixture was heated to 72° C. for 30 seconds and subsequently spray-dried to generate a spray-dried infant formula powder. This infant formula powder was mixed with non-denatured lactoferrin to provide 0.05 g non-denatured lactoferrin per 100 ml infant formula after reconstitution.

The infant formula was provided as a powder with the instruction to reconstitute with water. About 13.2 g powder was reconstituted to 100 ml ready to drink infant formula.

The invention claimed is:

1. A method for reducing the risk of developing or treating an allergic response to an allergen originating from food in an infant or a toddler comprising administering to the infant or toddler a nutritional composition comprising 0.03-14 wt % non-denatured lactoferrin, calculated by weight of total protein within the nutritional composition, said nutritional composition being selected from infant formula, follow-on formula and growing-up milk, wherein the infant or toddler is allergen sensitized and, wherein the nutritional composition comprises 5-20 cal. % protein, 30-60 cal. % lipids, and 25-75 cal. % digestible carbohydrates; wherein the protein comprises the non-denatured lactoferrin.

2. The method according to claim 1, wherein the nutritional composition contains 0.06-11 wt. % non-denatured lactoferrin, calculated by weight of total protein within the nutritional composition.

3. The method according to claim 1, wherein at least 70 wt. % of the total lactoferrin in the nutritional composition is non-denatured lactoferrin.

4. The method according to claim 1, wherein the nutritional composition is a powder.

5. The method according to claim 4, wherein the powder is reconstituted with aqueous liquid to prepare a reconstituted liquid formula and wherein the reconstituted liquid formula is subsequently orally administered to the infant or the toddler.

6. The method according to claim 5, wherein the reconstituted liquid formula comprises 0.005 to 2 g/L of non-denatured lactoferrin.

7. The method according to claim 1, wherein the non-denatured lactoferrin is isolated from milk of a non-human animal or produced by a genetically modified organism.

8. The method according to claim 1, wherein the method is for reducing the risk of developing or treating an IgE-mediated allergy.

9. The method according to claim 1, wherein the reducing the risk of developing or treating an allergic response to an allergen originating from feed-non-dairy food.

10. The method according to claim 1, wherein the reducing the risk of developing or treating an allergic response is for an allergen selected from peanut, tree nut, shell fish, wheat, soy, egg, sesame, and mold.

11. The method according to claim 1, wherein the nutritional composition is not fermented.

12. The method according to claim 1, wherein the nutritional composition is prepared by a process comprising the steps of:

a) providing a mixture of protein, lipids and digestible carbohydrates;

b) heating said mixture to at least 72° C. to obtain a heated mixture;

c) spray drying said heated mixture to obtain a powdered composition; and d) dry-blending non-denatured lactoferrin with the powdered composition to obtain the nutritional composition.

13. The method according to claim 2, wherein the nutritional composition contains 0.12-6 wt. % non-denatured lactoferrin, calculated by weight of total protein within the nutritional composition.

14. The method according to claim 3, wherein at least 90 wt. % of the total lactoferrin in the nutritional composition is non-denatured lactoferrin.

15. The method according to claim 6, wherein the reconstituted liquid formula comprises 0.02 to 0.8 g/L of non-denatured lactoferrin.

16. The method according to claim 7, wherein the non-denatured lactoferrin is non-denatured bovine, caprine or ovine lactoferrin.

* * * * *